United States Patent
Tomisawa et al.

(10) Patent No.: US 7,279,584 B2
(45) Date of Patent: Oct. 9, 2007

(54) METHOD FOR PRODUCTION OF CIS-4-FLUORO-L-PROLINE DERIVATIVES

(75) Inventors: Kazuyuki Tomisawa, Saitama (JP); Dai Tatsuta, Tokyo (JP); Tomomichi Yoshida, Tokyo (JP); Chihiro Yokoo, Tokyo (JP)

(73) Assignee: Taisho Pharmaceutical Co., Ltd., Tokyo (JP)

( * ) Notice: Subject to any disclaimer, the term of this patent is extended or adjusted under 35 U.S.C. 154(b) by 0 days.

(21) Appl. No.: 10/568,708

(22) PCT Filed: Aug. 18, 2004

(86) PCT No.: PCT/JP2004/011827

§ 371 (c)(1), (2), (4) Date: Aug. 4, 2006

(87) PCT Pub. No.: WO2005/016880

PCT Pub. Date: Feb. 24, 2005

(65) Prior Publication Data

US 2006/0281927 A1   Dec. 14, 2006

(30) Foreign Application Priority Data

Aug. 18, 2003 (JP) ............................. 2003-207718

(51) Int. Cl.
C07D 207/16 (2006.01)
(52) U.S. Cl. ...................... 548/532; 548/533
(58) Field of Classification Search ................ 548/532, 548/533
See application file for complete search history.

(56) References Cited

U.S. PATENT DOCUMENTS 6,384,234 B1 * 5/2002 Taylor et al. ............... 548/453

FOREIGN PATENT DOCUMENTS

JP  2002-275267 A   9/2002
JP  WO-2006/103986   * 10/2006

OTHER PUBLICATIONS

L. Demange, et al., "Practical Synthesis of Boc and Fmoc Protected 4-Fluoro and 4-Difluoroprolines from Trans-4-Hydroxyproline," Tetrahedron Letters, 1998, pp. 1169-1172, vol. 39, France.
G. Giardina, et al., "Facile and Efficient Syntheses of Novel (S)- and (R)-3-Fluoropyrrolidines and 3,3-Difluoropyrrolidine," Synlett, Jan. 1995, pp. 55-57, No. 5, Italy.

* cited by examiner

Primary Examiner—Fiona T Powers
(74) Attorney, Agent, or Firm—Sughrue Mion, PLLC

(57) ABSTRACT

The present invention provides a safer method for production of a cis-4-fluoro-L-proline derivative under milder conditions and in good yield to give a product of high purity on an industrial scale at low cost. Namely, the present invention provides a method for producing a cis-4-fluoro-L-proline derivative, which comprises reacting a trans-4-hydroxy-L-proline derivative of the following Formula [I]:

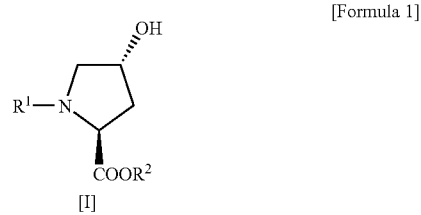

[Formula 1]

[I]

(wherein $R^1$ represents a protecting group for an α-amino group, and $R^2$ represents a protecting group for a carboxyl group) with N,N-diethyl-N-(1,1,2,3,3,3-hexafluoropropyl) amine in the presence of a hydrogen fluoride-scavenger.

7 Claims, No Drawings

METHOD FOR PRODUCTION OF CIS-4-FLUORO-L-PROLINE DERIVATIVES

This is a National Stage of International Application No. PCT/2004/011827, filed Aug. 18, 2004.

TECHNICAL FIELD

The present invention relates to a method for producing a cis-4-fluoro-L-proline derivative that is useful as a synthetic intermediate for pharmaceutical preparations and agricultural chemicals.

BACKGROUND ART

A cis-4-fluoro-L-proline derivative can be prepared from a trans-4-hydroxy-L-proline derivative through fluorination of its hydroxyl group at the 4-position. However, conventional fluorination techniques have posed various problems, as explained below.

The first method for fluorination is a method which uses diethylaminosulfur trifluoride (DAST). This method provides a target product in good yield, but is unsuitable for industrial use because DAST is highly toxic and less heat stable, as well as being explosive and expensive (Luc Demange et al., Tetrahedron Lett., 39, 1169 (1998)).

The second method is a method in which the hydroxyl group at the 4-position is converted into a leaving group and then into a fluoro group (G. Giardina et al., Synlett, 1, 55 (1995)). This method is of limited practical use because the yield of a target product is reduced as a result of olefin generation caused by β-elimination of the leaving group.

The third method is a method which uses N,N-diethyl-N-(1,1,2,3,3,3-hexafluoropropyl)amine (hereinafter referred to as "Ishikawa reagent"). This method is considered to be excellent in that it has a reduced risk of explosion, is available at low cost and enables the introduction of a fluoro group in a single step. However, there is a problem of reduced yield of a target compound because hydrogen fluoride generated during the reaction causes not only erosion of reaction vessels, but also decomposition of starting materials and reaction products. Moreover, particularly in the case of using a urethane-type protecting group which is widely used as a protecting group for an amino group in an α-amino acid, this protecting group will be easily decomposed by the action of hydrogen fluoride and hence requires the limited reaction conditions (e.g., at low temperature over a long period of time), thus failing to produce satisfactory results in terms of yield, etc.

DISCLOSURE OF THE INVENTION

Problem to be Solved by the Invention

The object of the present invention is to provide a method which is safer than conventional fluorination techniques used for trans-4-hydroxy-L-proline derivatives and which enables industrial production of a target compound in high yield while avoiding side reactions.

Means for Solving the Problem

As a result of extensive and intensive efforts made to achieve the above object, the inventors of the present invention have found a practical production method in which a trans-4-hydroxy-L-proline derivative is reacted with Ishikawa reagent in the presence of a hydrogen fluoride-scavenger to obtain a cis-4-fluoro-L-proline derivative with high stereoselectivity and in good yield while avoiding side reactions, as compared to conventional techniques. This finding led to the completion of the present invention. The inventors have also found that even in the case of an amino acid substrate having a urethane-type protecting group for an α-amino group, the present invention can be applied under mild conditions while effectively avoiding side reactions.

Namely, one embodiment of the present invention is directed to a method for producing a cis-4-fluoro-L-proline derivative of Formula [II], which comprises reacting a trans-4-hydroxy-L-proline derivative of Formula [I]:

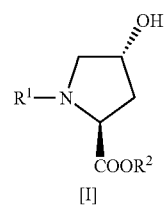

[Formula 1]

[I]

(wherein $R^1$ represents a protecting group for an α-amino group, and $R^2$ represents a protecting group for a carboxyl group) with N,N-diethyl-N-(1,1,2,3,3,3-hexafluoropropyl)amine in the presence of a hydrogen fluoride-scavenger to obtain the cis-4-fluoro-L-proline derivative of Formula [II]:

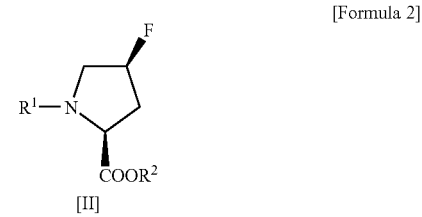

[Formula 2]

[II]

(wherein $R^1$ and $R^2$ are as defined above).

According to another embodiment of the present invention, there is provided such a method wherein the protecting group for an α-amino group is an aromatic urethane-type protecting group, an aliphatic urethane-type protecting group, a cycloalkylurethane-type protecting group, an acyl-type protecting group, a sulfonyl-type protecting group or an alkyl-type protecting group, and the protecting group for a carboxyl group is a $C_1$-$C_4$ alkyl group which may be substituted with a halogen atom(s), or a benzyl, allyl, phenacyl or benzhydryl group which may be substituted with a substituent(s) selected from the group consisting of $C_1$-$C_4$ alkoxy groups, $C_1$-$C_4$ alkyl groups, nitro groups and halogen atoms.

According to another embodiment of the present invention, there is provided such a method wherein the protecting group for an α-amino group is a benzyloxycarbonyl group, a tert-butoxycarbonyl group, a 4-methoxybenzyloxycarbonyl group, a 9-fluorenylmethyloxycarbonyl group, an allyloxycarbonyl group, a formyl group, an acetyl group, a phthaloyl group or a trityl group, and the protecting group for a carboxyl group is a methyl group, an ethyl group, a tert-butyl group, a benzyl group, a 4-methoxybenzyl group, a 4-nitrobenzyl group, an allyl group, a phenacyl group, a trichloroethyl group or a benzhydryl group.

According to another embodiment of the present invention, there is provided any one of the methods shown above wherein the hydrogen fluoride-scavenger is an alkali metal salt of fluorine.

According to another embodiment of the present invention, there is provided any one of the methods shown above wherein the hydrogen fluoride-scavenger is sodium fluoride.

According to another embodiment of the present invention, there is provided any one of the methods shown above wherein the reaction solvent is an inert solvent.

According to another embodiment of the present invention, there is provided any one of the methods shown above wherein the reaction solvent is dichloromethane.

When the hydroxyl group at the 4-position of a trans-4-hydroxy-L-proline derivative is fluorinated with Ishikawa reagent alone, the generated hydrogen fluoride causes decomposition of starting materials and reaction products, as described above. In particular, a urethane-type protecting group for an α-amino group (e.g., a tert-butoxycarbonyl group, a 4-methoxybenzyloxycarbonyl group) will be easily decomposed and hence greatly reduces product yield and purity. The present invention is characterized in that the hydroxyl group at the 4-position of a trans-4-hydroxy-L-proline derivative is fluorinated with Ishikawa reagent in the presence of a hydrogen fluoride-scavenger, with the aim of trapping hydrogen fluoride generated during the reaction in order to not only avoid erosion of reaction vessels, but also effectively prevent the above reaction.

The effect of the present invention to avoid side reactions allows fluorination of the hydroxyl group at the 4-position of a trans-4-hydroxy-L-proline derivative even at room temperature and higher temperatures where the fluorination is difficult to obtain when using Ishikawa reagent alone. The elevated reaction temperature also allows a reduction of the reaction time. Moreover, even when using a reduced amount of Ishikawa reagent, the inventors have succeeded in obtaining a cis-4-fluoro-L-proline derivative with high stereoselectivity and in good yield. By optimizing the reaction conditions, a target compound can be obtained with a very high degree of efficiency and in high yield.

The present invention will be illustrated in detail below, but is not limited to the particular embodiments described herein.

The term "protecting group for an α-amino group" refers to any group serving as a protecting group in each reaction, including those of urethane type, acyl type or sulfonyl type, as exemplified by aromatic urethane-type protecting groups (e.g., a benzyloxycarbonyl group (Z), a 2-chloro-benzyloxycarbonyl group, a 9-fluorenylmethyloxycarbonyl group, an isonicotinyloxycarbonyl group, a 4-methoxybenzyloxycarbonyl group), aliphatic urethane-type protecting groups (e.g., a tert-butoxycarbonyl group (Boc), t-amyloxycarbonyl (Aoc), an isopropyloxycarbonyl group, a 2-(4-biphenyl)-2-propyloxycarbonyl group, an allyloxycarbonyl group, a methylsulfonylethoxycarbonyl group), cycloalkylurethane-type protecting groups (e.g., an adamantyloxycarbonyl group, a cyclopentyloxycarbonyl group, a cyclohexyloxycarbonyl group, an isobonyloxycarbonyl group), acyl-type protecting groups or sulfonyl-type protecting groups (e.g., trifluoroacetyl, an o-nitrophenylsulfenyl group, a formyl group, an acetyl group, a phthaloyl group), and alkyl-type protecting groups [e.g., a trityl group, a diphenylmethyl group, a $C_1$-$C_6$ alkyl group (e.g., a methyl group, a t-butyl group)]. Preferred are a benzyloxycarbonyl group, a tert-butoxycarbonyl group, a 4-methoxybenzyloxycarbonyl group, a 9-fluorenylmethyloxycarbonyl group and an allyloxycarbonyl group.

The term "protecting group for a carboxyl group" refers to any group serving as a protecting group in each reaction, as exemplified by a $C_1$-$C_4$ alkyl group which may be substituted with a halogen atom(s) (e.g., a methyl group, an ethyl group, a tert-butyl group, a trichloroethyl group), or a benzyl group, an allyl group, a phenacyl group or a benzhydryl group, each of which may be substituted with a substituent(s) selected from the group consisting of $C_1$-$C_4$ alkoxy groups, $C_1$-$C_4$ alkyl groups, nitro groups and halogen atoms (e.g., a benzyl group, a 4-methoxybenzyl group, a 4-nitrobenzyl group). Preferred is a $C_1$-$C_4$ alkyl group (e.g., a methyl group, an ethyl group, a tert-butyl group).

The hydrogen fluoride-scavenger is preferably an alkali metal salt of fluorine. Examples include sodium fluoride, potassium fluoride, cesium fluoride and rubidium fluoride, with sodium fluoride being more preferred.

MODE FOR CARRYING OUT THE INVENTION

A trans-4-hydroxy-L-proline derivative used as a starting material can be synthesized by reference to the procedure described in, e.g., Tetrahedron Letters 31(51), 7403-7406 (1990) or Tetrahedron Letters 39(10), 1169-1172 (1998).

In the present invention, a cis-4-fluoro-L-proline derivative can be obtained by reacting a trans-4-hydroxy-L-proline derivative with N,N-diethyl-N-(1,1,2,3,3,3-hexafluoropropyl)amine ("Ishikawa reagent") in the presence of a hydrogen fluoride-scavenger. In this case, the hydrogen fluoride-scavenger and Ishikawa reagent are preferably added sequentially in this order, i.e., the hydrogen fluoride-scavenger is preferably added prior to the addition of Ishikawa reagent. These reagents are added preferably under cooling conditions, followed by warming the reaction mixture to an appropriate reaction temperature.

The reaction solvent is preferably an inert solvent that does not affect the reaction, as exemplified by halogenated solvents (e.g., dichloromethane, chloroform, 1,2-dichloroethane), hydrocarbon solvents (e.g., benzene, toluene), ester solvents (e.g., ethyl acetate) and acetonitrile. More preferred is dichloromethane. The reaction temperature may be selected, as appropriate, from the range between 0° C. and the reflux temperature of the reaction solvent. The temperature is preferably 0° C. to 40° C., more preferably 10° C. to 30° C., and even more preferably 20° C. to 30° C.

The amount of Ishikawa reagent ranges from 1 to 3 equivalents, desirably 1.1 to 1.9 equivalents, and more desirably 1.1 to 1.3 equivalents, relative to a trans-4-hydroxy-L-proline derivative. The amount of the hydrogen fluoride-scavenger ranges from 1 to 3 equivalents, desirably 1.1 to 1.9 equivalents, and more desirably 1.1 to 1.3 equivalents, relative to a trans-4-hydroxy-L-proline derivative. The amount of the hydrogen fluoride-scavenger is preferably equivalent to or greater than that of Ishikawa reagent.

The endpoint of the reaction may be determined by monitoring the disappearance of the starting material trans-4-hydroxy-L-proline derivative by thin-layer chromatography or high performance liquid chromatography.

EXAMPLES

The method of the present invention will be further described in more detail by way of the following examples, which are not intended to limit the scope of the invention. "Ishikawa reagent" denotes N,N-diethyl-N-(1,1,2,3,3,3-hexafluoropropyl)amine.

Example 1

Synthesis of methyl(2S,4S)-1-(tert-butoxycarbonyl)-4-fluoropyrrolidine-2-carboxylate

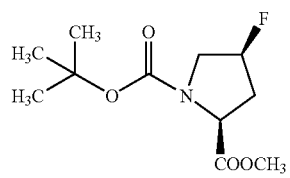

[Formula 3]

Methyl(2S,4R)-1-(tert-butoxycarbonyl)-4-hydroxypyrrolidine-2-carboxylate (4.91 g, 0.020 mol) and sodium fluoride (1.01 g, 0.024 mol) were suspended in dichloromethane (50 mL), followed by addition of Ishikawa reagent (4.35 mL, 0.024 mol) under ice cooling. The reaction mixture was slowly warmed to room temperature and then stirred for 20 hours. After the reaction, the reaction mixture was poured into ice-cold saturated aqueous sodium bicarbonate (70 mL) and then separated into organic and aqueous layers. The aqueous layer was extracted with ethyl acetate. This extracted solution was combined with the organic layer obtained above, washed sequentially with 10% aqueous potassium bisulfate and saturated aqueous sodium chloride, and then dried over anhydrous sodium sulfate. After drying, the solvent and the decomposition product of Ishikawa reagent (N,N-diethyl-2,3,3,3-tetrafluoropropionamide) were distilled off under reduced pressure, and the residue was applied to silica gel column chromatography (developing solvent; hexane:ethyl acetate=5:1 to 0:1) to give the titled compound (4.61 g, colorless oil).

ESI-MS: m/z 270 ([M+Na]$^+$).

$^1$H-NMR(CDCl$_3$): δ (ppm) 5.21(dm, J=52.5 Hz, 1H), 4.60-4.35(m, 1H), 3.74(s, 3H), 3.95-3.35(m, 2H), 2.60-2.10 (m, 2H), 1.50(s, minor conformer) and 1.42(s, major conformer) (9H).

Example 2

Synthesis of methyl(2S,4S)-1-benzyloxycarbonyl-4-fluoropyrrolidine-2-carboxylate

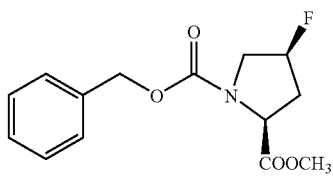

[Formula 4]

Methyl(2S,4R)-1-benzyloxycarbonyl-4-hydroxypyrrolidine-2-carboxylate (306 mg, 0.00108 mol) and sodium fluoride (55 mg, 0.00131 mol) were suspended in dichloromethane (1.8 mL), followed by addition of Ishikawa reagent (293 mg, 0.00131 mol) under ice cooling. The reaction mixture was slowly warmed to room temperature and then stirred for 20 hours. After the reaction, the reaction mixture was poured into ice-cold saturated aqueous sodium bicarbonate (5 mL) and then separated into organic and aqueous layers. The aqueous layer was extracted with ethyl acetate. This extracted solution was combined with the organic layer obtained above, washed sequentially with 10% aqueous potassium bisulfate and saturated aqueous sodium chloride, and then dried over anhydrous sodium sulfate. After drying, the solvent and the decomposition product of Ishikawa reagent (N,N-diethyl-2,3,3,3-tetrafluoropropionamide) were distilled off under reduced pressure, and the residue was applied to silica gel column chromatography (developing solvent; hexane:ethyl acetate=5:1 to 0:1) to give the titled compound (227 mg, colorless oil).

ESI-MS: m/z 304([M+Na]$^+$).

$^1$H-NMR(CDCl$_3$): δ (ppm) 7.41-7.25(m, 5H), 5.33-5.06 (m, 3H), 4.65-4.50(m, 1H), 3.75(s, 1.5H) and 3.65(s, 1.5H), 3.97-3.60(m, 2H), 2.61-2.21(m, 2H).

COMPARATIVE EXAMPLE

Methyl(2S,4R)-1-(tert-butoxycarbonyl)-4-hydroxypyrrolidine-2-carboxylate, a trans-4-hydroxy-L-proline derivative, was fluorinated at its 4-position using Ishikawa reagent alone or in combination with a hydrogen fluoride-scavenger. The results of the comparison between these two cases are shown below. The same procedure as used in Example 1 was repeated except for the conditions indicated in the following table. For reference purposes, the fluorination yield of the same compound is 81% when using diethylaminosulfur trifluoride (Tetrahedron Letters 39(10), 1169-1172 (1998)).

TABLE 1

| Entry | Ishikawa reagent (molar equivalents) | Reaction temperature (° C.) | Reaction time (hrs) | Hydrogen fluoride-scavenger (molar equivalents) | Yield (%) |
|---|---|---|---|---|---|
| 1 | 1.9 | 12 | 20 | None | 14 |
| 2 | 1.9 | 12 | 20 | NaF (1.9) | 85 |
| 3 | 1.2 | 21 | 8 | NaF (1.2) | 85 |

The present invention enables the production of a target cis-4-fluoro-L-proline derivative in good yield and under mild conditions while avoiding side reactions. The method of the present invention is therefore an excellent method which enables the provision of a cis-4-fluoro-L-proline derivative in high yield and on an industrial scale, as compared to conventional techniques.

REFERENCE EXAMPLE

Starting with methyl(2S,4S)-1-(tert-butoxycarbonyl)-4-fluoropyrrolidine-2-carboxylate obtained in the present invention, the following reference example shows the synthesis of (2S,4S)-4-fluoro-1-{[(2-hydroxy-1,1-dimethylethyl)amino]acetyl}pyrrolidine-2-carbonitrile monobenzenesulfonate salt, which is a cyanopyrrolidine derivative having inhibitory activity against dipeptidyl peptidase IV (DPPIV).

I. Synthesis of (2S,4S)-1-(tert-butoxycarbonyl)-4-fluoropyrrolidine-2-carboxylic acid Methyl(2S,4S)-1-(tert-butoxycarbonyl)-4-fluoropyrrolidine-2-carboxylate (5.00 g) was dissolved in methanol (30 mL). While stirring this solution under ice cooling, 5 mol/L aqueous sodium hydroxide (12 mL) was gradually added dropwise. After stirring at room temperature for 2 hours, the reaction mixture was evaporated under reduced pressure to remove methanol. The resulting residue was washed with diethyl ether, diluted with 10% aqueous potassium bisulfate (70 mL), and then extracted with ethyl acetate. The extracted solution was washed with water and saturated aqueous sodium chloride, dried over anhydrous sodium sulfate, and then concentrated under reduced pressure. Diisopropyl ether (20 mL) was added to the resulting residue and the precipitated crystal was collected by filtration to give the titled compound (3.91 g, white powder).

Melting point: 158-159° C.

ESI-MS: m/z 256([M+Na]$^+$).

$^1$H-NMR(DMSO-d$_6$): δ (ppm) 12.55(brs, 1H), 5.24(dm, J=54.4 Hz, 1H), 4.27(dd, J=9.3, 9.0, 1H), 3.69-3.47(m, 2H), 2.61-2.31(m, 2H), 2.30-2.15(m, 1H), 1.41(s, minor conformer) and 1.36(s, major conformer)(9H).

II. Synthesis of (2S,4S)-1-(tert-butoxycarbonyl)-2-carbamoyl-4-fluoropyrrolidine (2S,4S)-1-(tert-Butoxycarbonyl)-4-fluoropyrrolidine-2-carboxylic acid (70.0 g) was dissolved in tetrahydrofuran (700 mL) and then cooled to −11° C. To this solution, triethylamine (33.4 g) and ethyl chlorocarbonate (35.8 g) were slowly added and stirred at −15° C. for 30 minutes. Subsequently, 28% aqueous ammonia (73 mL) was added to the reaction mixture. After stirring at −10° C. for 40 minutes, a mixture of ethyl acetate and tetrahydrofuran (4:1, 1400 mL) and water (230 mL) were added and stirred. The reaction mixture was separated into organic and aqueous layers, and the aqueous layer was further extracted with a mixture of ethyl acetate and tetrahydrofuran (4:1, 350 mL). The combined organic layers were washed sequentially with 10% aqueous potassium bisulfate and saturated aqueous sodium chloride, dried over anhydrous sodium sulfate, and then concentrated under reduced pressure. The resulting crude crystal was recrystallized from a mixed solvent of acetonitrile and diisopropyl ether to give the titled compound (57.7 g, white powder).

Melting point: 172-173° C.

ESI-MS: m/z 255([M+Na]$^+$).

$^1$H-NMR(DMSO-d$_6$): δ (ppm) 7.21(brs, major conformer) and 7.15(brs, minor conformer)(1H), 6.94(brs, 1H), 5.21(dm, J=54.1 Hz, 1H), 4.13(d, J=9.6 Hz, 1H), 3.70-3.45 (m, 2H), 2.56-2.24(m, 1H), 2.24-2.08(m, 1H), 1.41(s, minor conformer) and 1.36(s, major conformer)(9H).

III. Synthesis of (2S,4S)-2-carbamoyl-4-fluoropyrrolidine hydrochloride salt (2S,4S)-1-(tert-Butoxycarbonyl)-2-carbamoyl-4-fluoropyrrolidine (122 g) was suspended in ethyl acetate (400 mL). While stirring this suspension under ice cooling, 4 mol/L hydrochloric acid-ethyl acetate (525 mL) was slowly added dropwise. After stirring at ice-cold temperature for 30 minutes and at room temperature for 3 hours, the precipitated crystal was collected by filtration to give the titled compound (85.9 g, white powder).

Melting point: 237-239° C. (decomposition).

ESI-MS: m/z 155([M+Na]$^+$).

$^1$H-NMR(DMSO-d$_6$): δ (ppm) 9.75(brs, 2H), 8.14(s, 1H), 7.72(s, 1H), 5.39(dm, J=52.4 Hz, 1H), 4.30(dd, J=10.5, 3.8 Hz, 1H), 3.66-3.22(m, 2H), 2.80-2.22(m, 2H).

IV. Synthesis of (2S,4S)-1-chloroacetyl-4-fluoropyrrolidine-2-carbonitrile (2S,4S)-2-Carbamoyl-4-fluoropyrrolidine hydrochloride salt (2.00 g) was suspended in dimethylformamide (20 mL). To this suspension, chloroacetyl chloride (1.48 g) and triethylamine (2.53 g) were added sequentially under ice cooling and stirred at ice-cold temperature for 30 minutes. Subsequently, cyanuric chloride (1.33 g) was added and stirred at ice-cold temperature for 30 minutes and at room temperature for 30 minutes. After the reaction mixture was poured into ice-cold water and stirred for 10 minutes, the precipitated crystal was collected by filtration to give the titled compound (1.76 g, white powder).

Melting point: 173-175° C.

ESI-MS: m/z 213([M+Na]$^+$).

$^1$H-NMR(DMSO-d$_6$): δ (ppm) 5.50(dm, J=51.9 Hz, 1H), 5.05-4.94(m, 1H), 4.52 and 4.39(ABq, J=14.3 Hz, 2H), 3.97(dd, J=24.8, 12.3 Hz, 1H), 3.75(ddd, J=39.2, 12.4, 3.3 Hz, 1H), 2.64-2.22(m, 2H).

V. Synthesis of (2S,4S)-4-fluoro-1-{[(2-hydroxy-1,1-dimethylethyl)amino]acetyl}pyrrolidine-2-carbonitrile (2S,4S)-1-Chloroacetyl-4-fluoropyrrolidine-2-carbonitrile (75.5 g) was suspended in isopropyl alcohol (1360 mL), followed by addition of 2-amino-2-methyl-1-propanol (88.0 g). After the reaction mixture was stirred at around 65° C. for 5.5 hours and overnight at room temperature, the precipitated crystal was collected by filtration to give the titled compound (66.6 g, white powder).

Melting point: 146-148° C.

ESI-MS: m/z 266([M+Na]$^+$).

$^1$H-NMR(DMSO-d$_6$): δ (ppm) 5.48(dm, J=51.9 Hz, 1H), 5.00-4.90(m, 1H), 4.65-4.55(m, 1H), 3.93(dd, J=24.7, 12.5 Hz, 1H), 3.72(ddd, J=39.7, 12.5, 3.4 Hz, 1H), 3.38 and 3.25(ABq, J=16.5 Hz, 2H), 3.20-3.12(m, 2H), 2.58-2.32(m, 2H), 1.92(brs, 1H), 0.94(s, 3H), 0.93(s, 3H).

VI. Synthesis of (2S,4S)-4-fluoro-1-{[(2-hydroxy-1,1-dimethylethyl)amino]acetyl}pyrrolidine-2-carbonitrile monobenzenesulfonate (2S,4S)-4-Fluoro-1-{[(2-hydroxy-1,1-dimethylethyl)amino]acetyl}pyrrolidine-2-carbonitrile (222 g) was suspended in methanol (3330 mL). While stirring this suspension at room temperature, a methanol solution of benzenesulfonic acid monohydrate (169 g) was gradually added dropwise. After the reaction mixture was stirred at room temperature for 15 minutes, isopropyl ether (3670 mL) was added and stirred at room temperature for 2.5 hours. The precipitated crystal was collected by filtration to give the titled compound (345 g, white powder).

Melting point: 220-221° C.

ESI-MS: m/z 266([M+Na]$^+$)(free base).

$^1$H-NMR(DMSO-d$_6$): δ (ppm) 8.61(brs, 2H), 7.63-7.57 (m, 2H), 7.36-7.28(m, 3H), 5.61-5.45(m, 1H), 5.47(d, J=5.2 Hz, 1H), 5.06(d, J=8.5 Hz, 1H), 4.10 and 3.88(ABq, J=16.6 Hz, 2H), 4.08(dd, J=24.4, 11.9 Hz, 1H), 3.78(ddd, J=39.6, 11.9, 3.4 Hz, 1H), 3.47(d,J=5.2 Hz, 1H), 2.68-2.35(m, 2H), 1.23(s, 3H), 1.22(s, 3H).

INDUSTRIAL APPLICABILITY

The present invention enables the conversion of a hydroxyl group at the 4-position of a proline derivative into a fluoro group under safe and mild conditions, in good yield and with high stereoselectivity. The present invention also enables the provision of a production method which allows fluorination to occur in good yield and the fluorinated compound to be supplied on an industrial scale, even in the case of using an amino acid substrate having a widely-used urethane-type protecting group for an α-amino group.

The invention claimed is:

1. A method for producing a cis-4-fluoro-L-proline derivative of Formula [II], which comprises reacting a trans-4-hydroxy-L-proline derivative of Formula [I]:

[Formula 1]

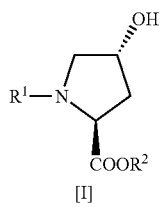

[I]

(wherein $R^1$ represents a protecting group for an α-amino group, and $R^2$ represents a protecting group for a carboxyl group) with N,N-diethyl-N-(1,1,2,3,3,3-hexafluoropropyl) amine in the presence of a hydrogen fluoride-scavenger and in the presence of a reaction solvent to obtain the cis-4-fluoro-L-proline derivative of Formula [II]:

[Formula 2]

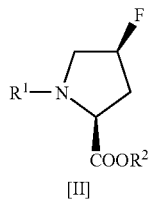

[II]

(wherein $R^1$ and $R^2$ are as defined above).

2. The method according to claim 1, wherein the protecting group for an α-amino group is an aromatic urethane-type protecting group, an aliphatic urethane-type protecting group, a cycloalkylurethane-type protecting group, an acyl-type protecting group, a sulfonyl-type protecting group or an alkyl-type protecting group, and the protecting group for a carboxyl group is a $C_1$-$C_4$ alkyl group which may be substituted with a halogen atom(s), or a benzyl, allyl, phenacyl or benzhydryl group which may be substituted with a substituent(s) selected from the group consisting of $C_1$-$C_4$ alkoxy groups, $C_1$-$C_4$ alkyl groups, nitro groups and halogen atoms.

3. The method according to claim 1, wherein the protecting group for an α-amino group is a benzyloxycarbonyl group, a tert-butoxycarbonyl group, a 4-methoxybenzyloxycarbonyl group, a 9-fluorenylmethyloxycarbonyl group, an allyloxycarbonyl group, a formyl group, an acetyl group, a phthaloyl group or a trityl group, and the protecting group for a carboxyl group is a methyl group, an ethyl group, a tert-butyl group, a benzyl group, a 4-methoxybenzyl group, a 4-nitrobenzyl group, an allyl group, a phenacyl group, a trichloroethyl group or a benzhydryl group.

4. The method according to any one of claims 1 to 3, wherein the hydrogen fluoride-scavenger is an alkali metal salt of fluorine.

5. The method according to claim 4, wherein the hydrogen fluoride-scavenger is sodium fluoride.

6. The method according to any one of claims 1 to 3, wherein the reaction solvent is an inert solvent.

7. The method according to claim 6, wherein the reaction solvent is dichloromethane.

* * * * *